US00PP19375P2

(12) United States Plant Patent
Egger

(10) Patent No.: US PP19,375 P2
(45) Date of Patent: Oct. 21, 2008

(54) ***HEUCHERA* PLANT NAMED 'GEORGIA PEACH'**

(50) Latin Name: *Heuchera hybrid*
Varietal Denomination: Georgia Peach

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/879,469

(22) Filed: Jul. 16, 2007

(51) Int. Cl.
*A01H 5/00* (2006.01)

(52) U.S. Cl. ..... Plt./440
(58) Field of Classification Search ..... Plt./440
See application file for complete search history.

*Primary Examiner*—Kent L. Bell
*Assistant Examiner*—June Hwu
(74) *Attorney, Agent, or Firm*—Klarquist Sparkman, LLP

(57) ABSTRACT

A new and distinct hybrid of *Heuchera* plant characterized by large leaves colored pink-orange shades in the spring and early summer changing to burgundy-pink shades in the fall and winter, strongly veiled foliage, cream colored flowers on reddish peduncles, excellent vigor, excellent tolerance to heat and humidity.

3 Drawing Sheets

Botanical denomination: *Heuchera* hybrid.
Variety designation: 'Georgia Peach'.

BACKGROUND OF THE INVENTION

The present invention relates to a new and distinct cultivar of *Heuchera* hybrid and given the cultivar name of 'Georgia Peach'. *Heuchera* is in the family Saxifragaceae. *Heuchera* 'Georgia Peach' originated from a cross between *Heuchera* V3, a proprietary non commercial *H. villosa* hybrid, as the seed parent, and *Heuchera* 647-5, a proprietary non commercial plant, as the pollen parent.

SUMMARY OF THE INVENTION

This new *Heuchera* is distinguished by:

1. Large leaves colored pink-orange shades in the spring and early summer changing to burgundy-pink shades in the fall and winter.
2. Strongly veiled foliage.
3. Cream colored flowers on reddish peduncles.
4. Excellent vigor.
5. Excellent tolerance to heat and humidity.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

DETAILED PLANT DESCRIPTION

Figure 1:
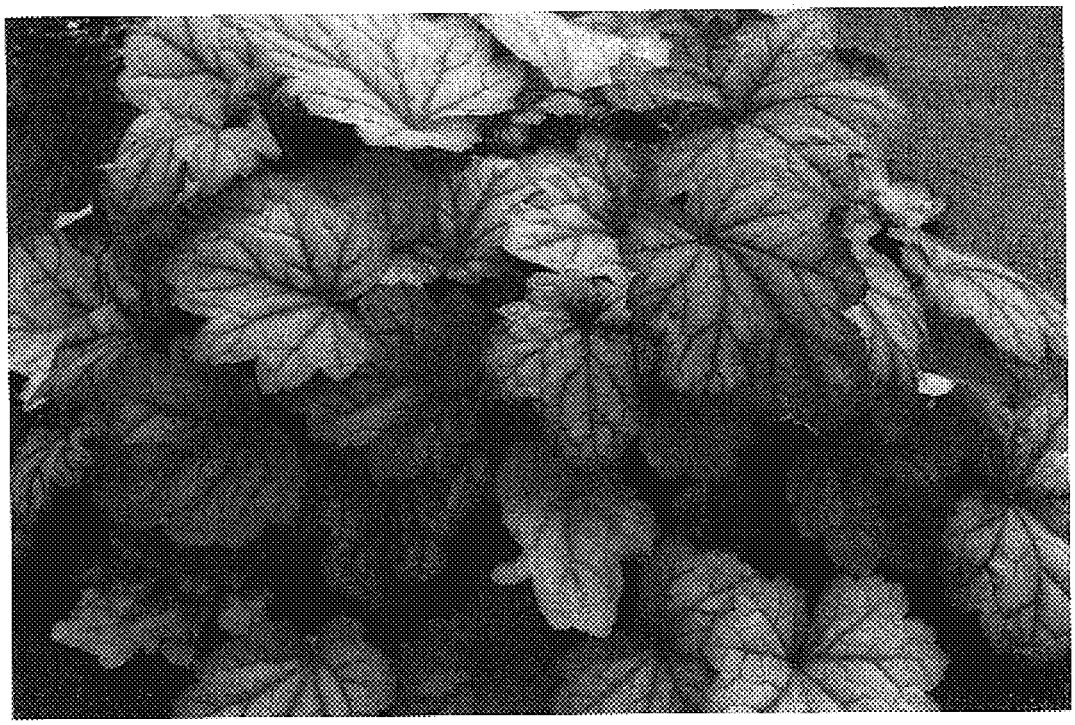
FIG. 1 shows a one-year-old plant of *Heuchera* 'Georgia Peach' growing in the ground in high shade in the trial field in April in Canby, Oreg.
Figure 2:
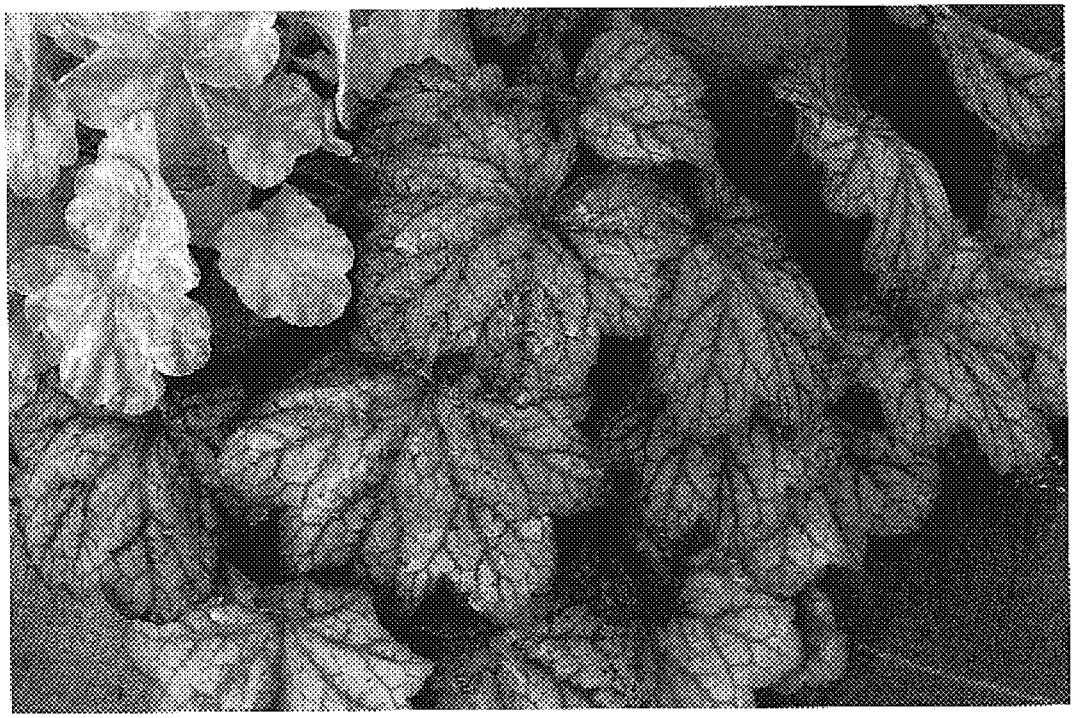
FIG. 2 is the same plant in August shown next to a lime colored *Heuchera*.
Figure 3:
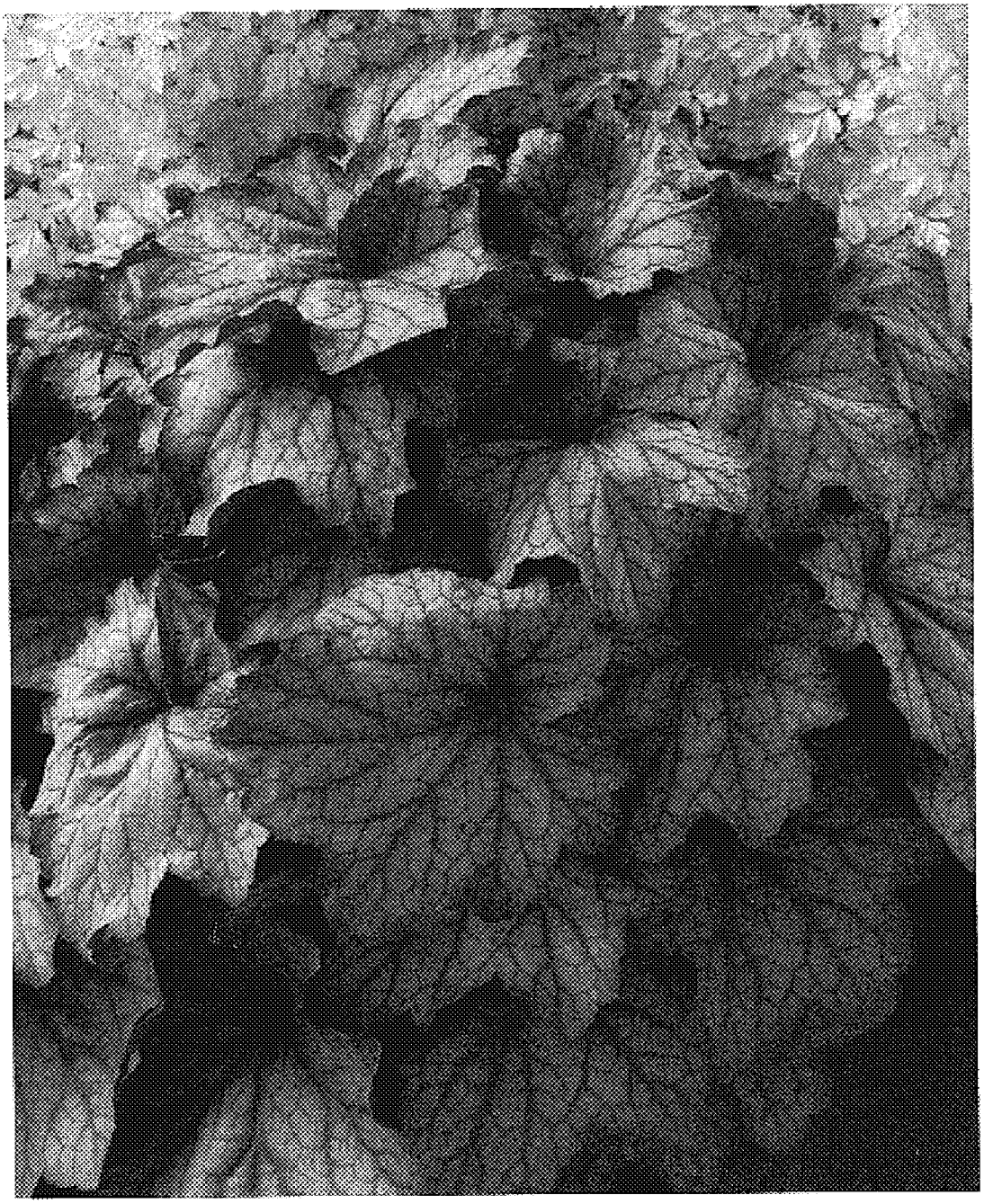
FIG. 3 is the same plant in October.
Figure 4:
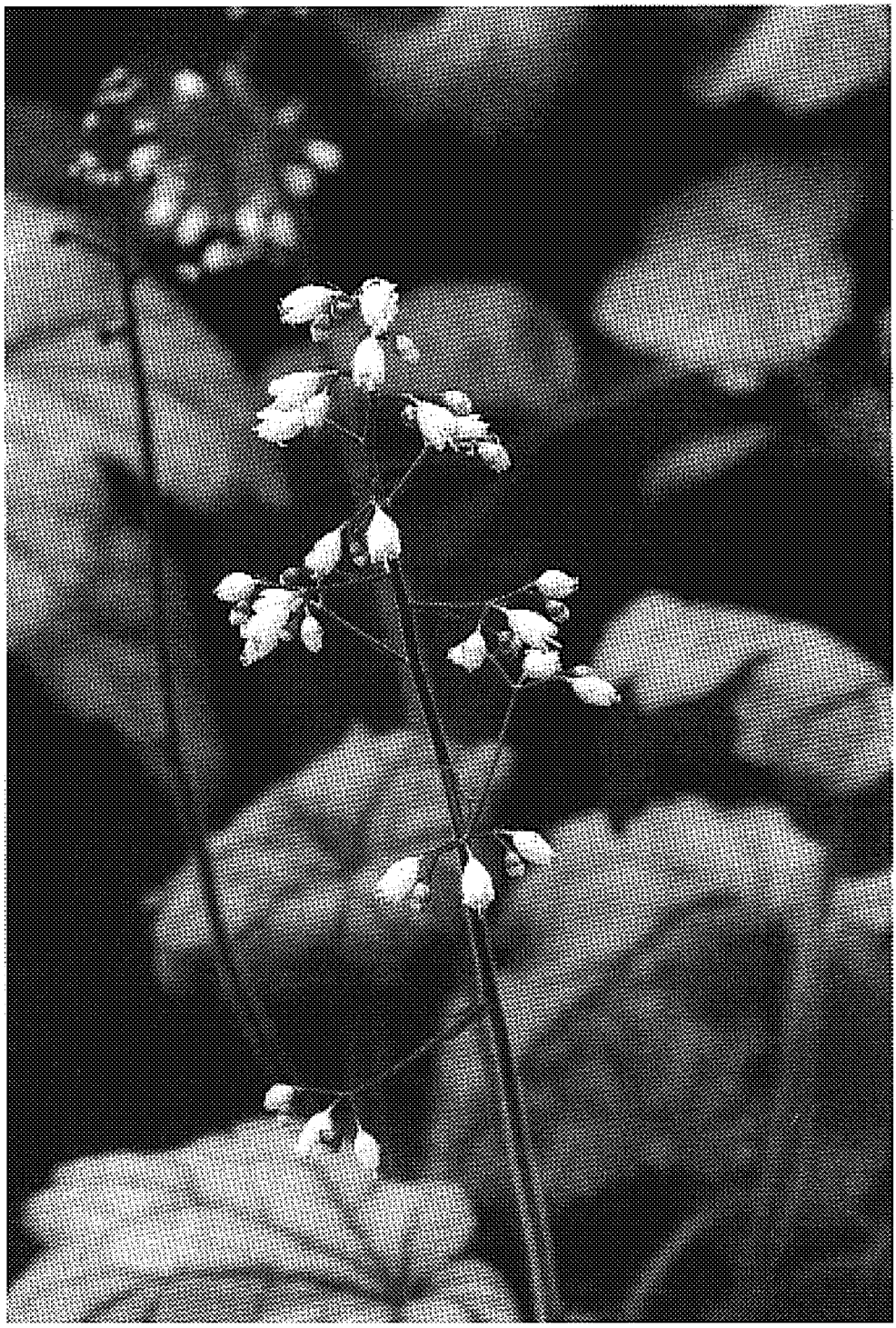
FIG. 4 shows a close up of the inflorescence in April in Canby, Oreg.

The following is a detailed description of the new *Heuchera* cultivar based on observations taken in May of a two-year-old specimen growing in the ground in the trial bed under high shade and with added irrigation in the summer months in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Form.*—Basal rosette, herbaceous perennial.
*Hardiness.*—USDA Zone 4 to 9.
*Size.*—20 cm tall from top of the foliage to the ground and 50 cm wide.
*Habit.*—Mounding.
*Vigor.*—Excellent.
*Roots.*—Fibrous, freely branching, fine, and white in color; roots develop easily from cuttings.

Leaf:

*Type.*—Simple.
*Arrangement.*—Rosette.
*Shape.*—Broadly ovate.
*Lobing/division.*—7 shallow lobes, the terminal is the longest.
*Venation.*—Palmate.
*Margins.*—Crenate.
*Apex.*—Mucronulate.
*Base.*—Cordate, lobes sometimes overlapping at the base.
*Blade size.*—10 to 13 cm long and 9 to 12.5 cm wide.

*Surface texture.*—Glandular on both sides.

*Texture.*—Thin, leathery.

*Petiole description.*—15 to 22 cm long and 2 mm wide, glandular hairs, closest to Greyed Purple 183C.

*Leaf color.*—Variable depending on season and age of the leaf, veins with strong colors and between the veins (interveinally) there is a heavy "silver" veil lightening the leaf color; summer leaves Greyed Purple 185A on the veins and closest to Greyed Purple 186A interveinally, mature leaves are Greyed Purple 185A on veins and between Greyed Red 182B and Greyed Purple 186C interveinally, older leaves are Greyed Red 182A and closest to Greyed Red 182C interveinally; mature leaves backside Greyed Purple 187C; spring leaves topside Greyed Orange 169A to 170B on leaf margins and veins, veil color closest to Greyed Red 182D and lighter, back side Greyed Purple 187D; winter leaves have more purple tones than summer leaves, topside veins closest to Red Purple 59C and veil is between 202A and Greyed Purple 186A, back side Greyed Purple 187C.

Inflorescence:

*Size.*—6 cm wide and 17 cm long.

*Type.*—Thyrse.

*Number of flowers per thyrse.*—About 75 per thyrse.

*Number of thyrse.*—5 in spring bloom.

*Peduncle.*—Grows to 55 cm tall, 4 mm wide at base, between Red Purple 59A and Greyed Purple 187A, prominent glandular hairs, with 1 to 2 petiolate cauline leaves (ovate, blades 2 to 5 cm long and 1 to 4 cm wide with a lobed and incised margin, between Red Purple 59A and Greyed Purple 187A).

*Pedicel.*—Variable in size, with glandular hairs, between Red Purple 59A and Greyed Purple 187A.

*Bloom period.*—Late May to June in Canby, Oreg.

Flower bud:

*Size.*—3 mm wide and 4 mm long.

*Description.*—Glandular puberulent, ovoid.

*Color.*—Red Purple 59D.

Flower:

*Type.*—Perfect.

*Shape.*—Campanulate.

*Size.*—5 mm long and 4 mm wide.

*Petal description.*—5 in number, inconspicuous, 2.5 mm long, spatulate, tip obtuse, margin entire, glandular on back side only, White 155A on inside and White 155A tinged Red Purple 62D at the tip on the back side.

*Calyx description.*—Campanulate, 5 mm long and 4 mm wide, with 5 lobes, divided ⅓ way to the base, glandular hairs, tip acute, margin entire, White 155A tinged Red Purple 62C on both sides, back side tips are Red Purple 71B.

*Stamen description.*—5 in number, filaments 3 mm long, White 155D, anthers sterile, 0.5 mm, Orange 26B.

*Pistil description.*—1, 2-beaked, 4 mm long, ovary 1 mm. Yellow White 158A, style 3 mm long, White 155D.

*Fragrance.*—None.

*Lastingness.*—Each thyrse blooms for about 2 weeks on the plant.

Fruit:

*Type.*—Two beaked capsule.

*Size.*—3.5 mm deep by 5 mm wide.

*Fertility.*—Good.

*Color.*—Brown 200D.

Seed:

*Shape.*—Linear.

*Size.*—2 mm long.

*Color.*—Black, RHS 202A.

Pest and disease tolerance: Excellent disease resistance to powdery mildew, the common problem of *Heuchera.* Susceptible to *Heuchera* rust and root weevils.

COMPARISON TO SIMILAR *HEUCHERA*

Compared to the seed parent, V-3, the new hybrid has leaves that are in warm, bright shades of peach to burgundy rather than dull amber to olive green shades.

Compared to the pollen parent 647-5, the new hybrid has leaves that are large rather than medium in size and in shades of warm, bright peach to burgundy rather than rose purple.

Compared to *Heuchera* 'Peach Flambé' (U.S. Plant Pat. No. 17,195) the new variety has a much different leaf color, pale ale to tan to olive green with a heavy silver white veil compared to an amber to olive green tone. The leaves of the new variety are larger and unruffled.

I claim:

1. A new and distinct hybrid of *Heuchera* plant as herein illustrated and described.

* * * * *